United States Patent
Wang et al.

(10) Patent No.: US 11,776,149 B2
(45) Date of Patent: *Oct. 3, 2023

(54) PREDICTION METHOD FOR HEALTHY RADIUS OF BLOOD VESSEL PATH, PREDICTION METHOD FOR CANDIDATE STENOSIS OF BLOOD VESSEL PATH, AND BLOOD VESSEL STENOSIS DEGREE PREDICTION DEVICE

(71) Applicant: KEYA MEDICAL TECHNOLOGY CO., LTD., Beijing (CN)

(72) Inventors: Xin Wang, Seattle, WA (US); Youbing Yin, Kenmore, WA (US); Junjie Bai, Seattle, WA (US); Yuwei Li, Bellevue, WA (US); Yi Lu, Seattle, WA (US); Kunlin Cao, Kenmore, WA (US); Qi Song, Seattle, WA (US)

(73) Assignee: KEYA MEDICAL TECHNOLOGY CO., LTD., Beijing (CN)

( * ) Notice: Subject to any disclaimer, the term of this patent is extended or adjusted under 35 U.S.C. 154(b) by 219 days.

This patent is subject to a terminal disclaimer.

(21) Appl. No.: 17/237,480

(22) Filed: Apr. 22, 2021

(65) Prior Publication Data
US 2021/0241484 A1 Aug. 5, 2021

Related U.S. Application Data

(63) Continuation of application No. 16/580,981, filed on Sep. 24, 2019, now Pat. No. 11,030,765.
(Continued)

(30) Foreign Application Priority Data

Apr. 2, 2019 (CN) .......................... 201910262838.0

(51) Int. Cl.
*G06T 7/62* (2017.01)
*G16H 30/20* (2018.01)
(Continued)

(52) U.S. Cl.
CPC ............ *G06T 7/62* (2017.01); *A61B 5/02007* (2013.01); *A61B 5/7264* (2013.01);
(Continued)

(58) Field of Classification Search
CPC . A61B 5/0022; A61B 5/02007; A61B 5/1075; A61B 5/7264; A61B 5/7267;
(Continued)

(56) References Cited

U.S. PATENT DOCUMENTS

2017/0265831 A1 9/2017 Sankaran et al.
2019/0318476 A1* 10/2019 Isgum ................ G06N 20/00

FOREIGN PATENT DOCUMENTS

CN 102258381 A 11/2011
WO 2017160994 A 9/2017

OTHER PUBLICATIONS

First Office action issued in related Chinese Application No. 201910262838.0, dated Sep. 14, 2020, 8 pages.

* cited by examiner

*Primary Examiner* — Manuchehr Rahmjoo
(74) *Attorney, Agent, or Firm* — Bayes PLLC

(57) ABSTRACT

A computer-implemented method for predicting a blood vessel stenosis is disclosed. The method may include extracting a blood vessel path and its centerline based on the image of the blood vessel. The method may further include determining a candidate stenosis for the blood vessel path and identifying image blocks along the centerline of the blood vessel path within a range of candidate stenosis for the blood vessel path determined based on the candidate steno-
(Continued)

sis. The method may also include determining a degree of stenosis for the blood vessel path by applying a trained learning network comprising a convolutional neural network and a recurrent neural network on the image blocks within the range of candidate stenosis.

20 Claims, 7 Drawing Sheets

Related U.S. Application Data

(60) Provisional application No. 62/735,829, filed on Sep. 24, 2018.

(51) Int. Cl.
*G16H 50/20* (2018.01)
*A61B 5/02* (2006.01)
*A61B 5/00* (2006.01)
*A61B 6/03* (2006.01)
*A61B 6/00* (2006.01)
*G06T 7/00* (2017.01)

(52) U.S. Cl.
CPC ............ *A61B 5/7275* (2013.01); *A61B 6/032* (2013.01); *A61B 6/504* (2013.01); *G06T 7/0014* (2013.01); *G16H 30/20* (2018.01); *G16H 50/20* (2018.01); *G06T 2207/10081* (2013.01); *G06T 2207/20021* (2013.01); *G06T 2207/20081* (2013.01); *G06T 2207/20084* (2013.01); *G06T 2207/30101* (2013.01); *G06T 2207/30172* (2013.01)

(58) Field of Classification Search
CPC ....... A61B 5/7275; A61B 6/032; A61B 6/504; A61B 6/507; A61B 6/5217; G06T 2207/10081; G06T 2207/20021; G06T 2207/20081; G06T 2207/20084; G06T 2207/30101; G06T 2207/30172; G06T 7/0012; G06T 7/0014; G06T 7/62; G16H 30/20; G16H 30/40; G16H 50/20; G16H 50/30
See application file for complete search history.

PREDICTION METHOD FOR HEALTHY RADIUS OF BLOOD VESSEL PATH, PREDICTION METHOD FOR CANDIDATE STENOSIS OF BLOOD VESSEL PATH, AND BLOOD VESSEL STENOSIS DEGREE PREDICTION DEVICE

CROSS-REFERENCE TO RELATED APPLICATION

This application is a continuation of U.S. application Ser. No. 16/580,981, filed Sep. 24, 2019, which claims the benefit of priority to U.S. Provisional Application No. 62/735,829, filed on Sep. 24, 2018, and Chinese Patent Application No. 2019102628380, filed on Apr. 2, 2019. The entire contents of all these priority applications are incorporated herein by reference.

TECHNICAL FIELD

The present disclosure relates to methods and devices for predicting blood vessel physiological parameters, for example to a method for predicting a healthy radius of a blood vessel path (a segment of a blood vessel), a method for predicting candidate stenosis of a blood vessel path, and a device for predicting the degree of blood vessel stenosis using machine learning.

BACKGROUND

Recent studies have shown that degree of blood vessel stenosis is of significance for the diagnosis and the prevention of cardiovascular disease. Generally, the degree of blood vessel stenosis is manually determined: the expert judges the degree of blood vessel stenosis by manual observation of coronary CT angiography (CTA) and/or quantitative coronary angiography (QCA). However, such judgment is time consuming, tedious, wastes huge amounts of resources, and relies heavily on the expert's experience.

Although some methods for automatically or semi-automatically determining the degree of vascular stenosis have been proposed, these methods either manually determine a detection area of degree of vascular stenosis by an expert or perform a global scan of a large section of blood vessels, wherein the former ones still rely heavily on expert's experience and the latter ones result in a large amount of computational resources being consumed and a slow computation speed, which does not satisfactorily meet clinical time requirements.

Traditional methods for automatically or semi-automatically determining blood vessel stenosis have also introduced machine learning, but these machine learning-based stenosis detection systems typically include multiple modules, such as a feature extraction module, a stenosis detection module and a stenosis weight estimation module. Generally, the feature extraction module manually specifies a feature extraction mode, which cannot be adaptively adjusted for different application scenarios. The stenosis detection module and the stenosis weight estimation module are independently trained, and the objective functions are different. The independent training of the modules requires corresponding training data, which has higher requirements for training data: the training cannot be complemented by cross-optimizing during the training process; and the optimal performance of the overall system cannot be achieved.

The present application has been proposed to solve the above-identified problems as well as for other purposes.

SUMMARY

Certain embodiments may provide an automated prediction method for the healthy radius of the blood vessel path implemented by a computer. The method does not rely on expert's experience and the predicted healthy radius agrees well with the actually measured healthy radius of the blood vessel path. Certain embodiments may provide a prediction method for the candidate stenosis of the blood vessel path implemented by a computer. The method does not rely on expert's experience to automatically and accurately determine candidate stenosis on the blood vessel path that requires further medical intervention. Certain embodiments may also or alternatively provide a blood vessel stenosis degree prediction device capable of automatically determining a candidate stenosis of the blood vessel path and detecting the degree of stenosis for candidate stenosis range of the blood vessel path, which can significantly reduce computation load and improve detection efficiency. At the same time, certain embodiments can effectively avoid missed detections. The device can realize the end-to-end detection of the stenosis from the image block sequence to the corresponding position of the entire blood vessel path by using the learning network. The training of the learning network may also be end-to-end mode. Training data sets may be easier to obtain and may enable a well-trained learning network to achieve good predictive performance of the device as a whole.

According to a first aspect of the present disclosure, there is provided a prediction method for a healthy radius of a blood vessel path, which is implemented by a computer, the predicting method including the steps of: acquiring a blood vessel radius of the blood vessel path; by a processor, detecting radius peak of the blood vessel radius of the blood vessel path; and by the processor, predicting the healthy radius of the blood vessel on the blood vessel path by performing regression on the radius peak of the blood vessel radius.

In some embodiments, the step of predicting the healthy radius of the blood vessel on the blood vessel path by performing regression on the radius peak of the blood vessel radius includes: predicting a reference healthy radius of the blood vessel on the blood vessel path by performing linear regression on the radius peak of the blood vessel radius; processing the radius peak in the blood vessel radius based on predicted reference healthy radius of the blood vessel on the blood vessel path; and predicting the healthy radius of the blood vessel on the blood vessel path by performing a quadratic regression on the processed radius peak in the vessel radius.

In some embodiments, the step of processing the radius peak in the blood vessel radius based on predicted reference healthy radius of the blood vessel on the blood vessel path includes: replacing the radius peak among the radius peaks of the blood vessel radius that is lower than the corresponding reference healthy radius with the corresponding reference healthy radius.

In some embodiments, the regression includes a Gaussian process regression.

According to a second aspect of the present disclosure, there is provided a prediction method for a candidate stenosis of a blood vessel path, which is implemented by a computer, the prediction method including: a prediction method for a healthy radius of a blood vessel path according to various embodiments of the present disclosure; by a processor, detecting a radius valley of a blood vessel radius on the blood vessel path; and by a processor, determining the candidate stenosis based on the radius valley and the healthy radius of the blood vessel path.

In some embodiments, the step of determining the candidate stenosis based on the radius valley and the healthy radius of the blood vessel path includes: determining a ratio of the radius valley to the healthy radius throughout the blood vessel path, and determining it as the candidate stenosis where the ratio is less than a first predetermined threshold; or determining a ratio of a difference between the healthy radius and a radius valley to a healthy radius throughout the blood vessel path, and determining it as the candidate stenosis where the ratio is greater than a second predetermined threshold.

In some embodiments, the regression includes a Gaussian process regression.

According to a third aspect of the present disclosure, a blood vessel stenosis degree prediction device is provided, the blood vessel stenosis degree prediction device includes: an interface configured to receive an image of a blood vessel; a memory storing executable instructions; a processor configured to implement following steps by executing the executable instructions: extracting a blood vessel path and its centerline based on an image of the blood vessel; determining candidate stenosis for each blood vessel path; setting a range of the candidate stenosis for each blood vessel path based on the determined candidate stenosis; obtaining image blocks along the centerline within the range of candidate stenosis for each of the blood vessel path; and based on the obtained image blocks, determining the degree of stenosis for each blood vessel path by using a trained learning network composed of a convolutional neural network and a recurrent neural network.

In some embodiments, the range of candidate stenosis for each blood vessel path is a length centered on the determined candidate stenosis.

In some embodiments, the candidate stenosis of each blood vessel path is determined by: obtaining a blood vessel radius of the blood vessel path; detecting a radius peak and a radius valley in a blood vessel radius of the blood vessel path; predicting reference healthy radius of the blood vessel path by performing linear regression on the radius peak in the blood vessel radius: replacing the radius peak among the radius peaks in the blood vessel radius that is lower than the corresponding reference healthy radius with the corresponding reference healthy radius; predicting the healthy radius of the blood vessel path by performing a quadratic regression on the replaced radius peak in the blood vessel radius; and determining the candidate stenosis based on the radius valley and the healthy radius of the blood vessel path.

In some embodiments, the step of determining the candidate stenosis based on the radius valley and the healthy radius of the blood vessel path includes: determining a ratio of the radius valley to the healthy radius throughout the blood vessel path, and determining it as the candidate stenosis where the ratio is less than a first predetermined threshold; or determining a ratio of a difference between the healthy radius and a radius valley to a healthy radius throughout the blood vessel path, and determining it as the candidate stenosis where the ratio is greater than a second predetermined threshold.

In some embodiments, the recurrent neural network is a bidirectional recurrent neural network.

In some embodiments, the blood vessel stenosis degree predicting device further includes: an output unit that is configured to output at least one of the stenosis, the range of stenosis, and the stenosis value, which may be a numeric representation of the degree of stenosis, of each blood vessel path.

According to a fourth aspect of the present disclosure, there is provided a non-transitory storage medium having stored thereon computer executable instructions that, when executed by a processor, implement at least one of the following methods: the prediction method for a healthy radius of a blood vessel path according to various embodiments of the present disclosure; the prediction method for a candidate stenosis of a blood vessel path according to various embodiments of the present disclosure; and a method for predicting a degree of stenosis of a blood vessel, the method including the steps of: extracting a blood vessel path and its centerline based on an image of the blood vessel; determining candidate stenosis for each blood vessel path; setting a range of the candidate stenosis for each blood vessel path based on the determined candidate stenosis; obtaining image blocks along the centerline within the range of the candidate stenosis for each blood vessel path; and based on the obtained image blocks, determining the degree of stenosis for each blood vessel path by using a trained learning network composed of a convolutional neural network and a recurrent neural network.

According to the prediction method for the healthy radius of the blood vessel path according to various embodiments of the present disclosure, it is possible to predict the healthy radius of the blood vessel path that is in good agreement with the actual situation. The prediction method for the candidate stenosis of the blood vessel path and the blood vessel stenosis degree prediction device according to various embodiments of the present disclosure can automatically determine the candidate stenosis and detect the degree of stenosis for the candidate stenosis range, which can significantly reduce the computation load, improve the detection efficiency, and effectively avoid missed detection.

BRIEF DESCRIPTION OF THE DRAWINGS

In the drawings, which are not necessarily drawn to scale, like reference numerals may describe similar components in different views. Like reference numerals having letter suffixes or different letter suffixes may represent different instances of similar components. The drawings illustrate generally, by way of example, but not by way of limitation, various embodiments, and together with the description and claims, serve to explain the disclosed embodiments.

DETAILED DESCRIPTION

The following technical terms have a uniform meaning in the present disclosure. The technical term "blood vessel path" refers to a path of a blood vessel from an inlet to an outlet; for example, a vessel tree may include multiple blood vessel paths. The technical term "blood vessel radius of a blood vessel path" means the radius of a blood vessel that is present throughout the blood vessel path, that is, a series of blood vessel radii corresponding to the radius of the blood vessel. The technical term "radius peak in the blood vessel radius of a blood vessel path" refers to a sequence of radius peaks in a series of vessel radii that are present throughout the blood vessel path.

Figure 1:
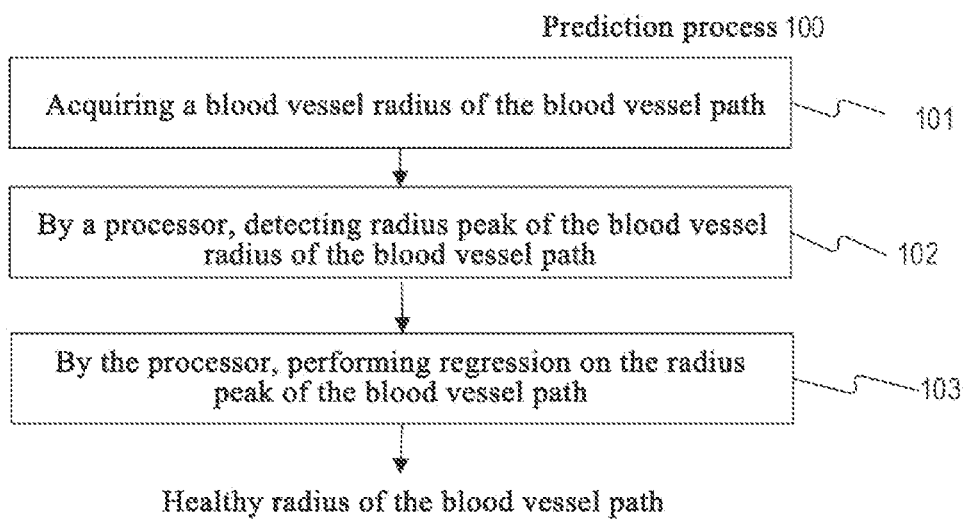
FIG. 1 illustrates a flow chart of a method for predicting a healthy radius of a blood vessel path in accordance with an embodiment of the present disclosure.

FIG. 1 shows an illustration of a process 100 of a method for predicting a healthy radius of a blood vessel path, in accordance with an embodiment of the present disclosure. As shown in FIG. 1, the prediction process 100 may start from acquiring a vessel radius of a blood vessel path (step 101). This step 101 can be implemented in various ways, for example, a device implementing the process can receive a medical image of a blood vessel collected by an image acquisition device, which can be a CT image taken along the longitudinal direction of the blood vessel, or digital subtraction angiography images at a number of different projection angles for the same blood vessel, etc. Then, based on the medical image of the collected blood vessel, various open source tools such as VMTK may be used to extract the center line and the blood vessel wall of the blood vessel path, thereby reconstructing a three-dimensional geometric model of the blood vessel, and extracting the radius of the blood vessel throughout the blood vessel path from the reconstructed three-dimensional geometric model, such as, but not limited to, the radius of the blood vessel throughout the centerline of the blood vessel path. Next, a processor may be used to detect a radius peak in a blood vessel radius of the blood vessel path (step 102). Specifically, among a series of blood vessel radii throughout the blood vessel path, a part of which is a local radius peak, and these local radius peaks are detected and arranged in order. Regression (step 103) may be performed on the sequence of these local radii peaks sequentially arranged by the processor to predict the healthy radius of the blood vessel path. This method for predicting the healthy radius can be automatically implemented, and the medical image of the blood vessel can be directly used as an input, which is friendly to the user and has a fast computation speed, and is in some extent compatible with the healthy radius distribution of the clinically detected blood vessel path.

In various embodiments in accordance with the present disclosure, the processor may be a processing device including one or more general purpose processing devices, such as a microprocessor, central processing unit (CPU), graphics processing unit (GPU), and the like. More specifically, the processor may be a Complex Instruction Set Computing (CISC) microprocessor, a Reduced instruction Set Computing (RISC) microprocessor, a Very Long Instruction Word (VLIW) microprocessor, a processor running other instruction sets or a processor that runs a combination of instruction sets. The processor may also be one or more dedicated processing devices such as an application specific integrated circuit (ASIC), field programmable gate array (FPGA), digital signal processor (DSP), system-on-chip (SoC), and the like. As will be appreciated by those skilled in the art, in some embodiments, the processor may be a dedicated processor rather than a general purpose processor. The processor may include one or more known processing devices such as a Pentium™, Core™, Xeon™ or Itanium series of microprocessors manufactured by Intel™, Turion™, Athlon™, Sempron™, Opteron™, FX™, Phenom™ series manufactured by AMD™, or various processors manufactured by Sun Microsystems. The processor may also include a graphics processing unit such as a GPU from GeForce®, Quadro® manufactured by Nvidia™, Tesla® series, GMA manufactured by Intel™, Iris™ series, or Radeon™ series manufactured by AMD™. The processor may also include an accelerated processing unit such as the Desktop A-4 (6, 6) series manufactured by AMD™ the Xeon Phi™ series manufactured by Intel™, and the like.

In some embodiments, regression may be implemented in various ways in step 103, including but not limited to spline fitting. Bayesian linear regression, piecewise binomial fitting, and the like. For example, Gaussian process regression can be used, and a kernel function may be introduced in the Gaussian process regression, so that the regression effect for the frequently fluctuated radius distribution curve of the blood vessel path is significantly better than other regression methods.

The various implementations of step 103 will be described below by taking Gaussian process regression as an example.

Figure 2A:
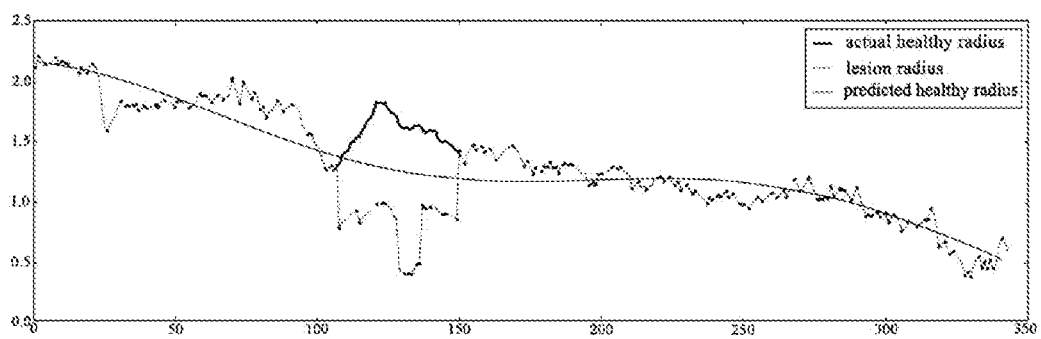
FIG. 2(a) shows a comparison of a healthy radius of a blood vessel diameter predicted by a first prediction method and actually measured healthy radius and lesion radius, in accordance with an embodiment of the present disclosure.

In some embodiments, a linear Gaussian process regression can be directly performed with the radius peak of the blood vessel path to predict the healthy radius of the blood vessel path, and the predicted healthy radius of the blood vessel path is shown by the solid line in FIG. 2(a). In FIG. 2(a), the distribution curve of the lesion radius of the blood vessel path is shown by a broken line, and the healthy radius actually measured when the lesion is not present in the current severely stenosis segment is shown by a bold line. It can be seen that the healthy radius of the predicted blood vessel path is relatively low compared with the actually measured healthy radius.

Figure 2B:
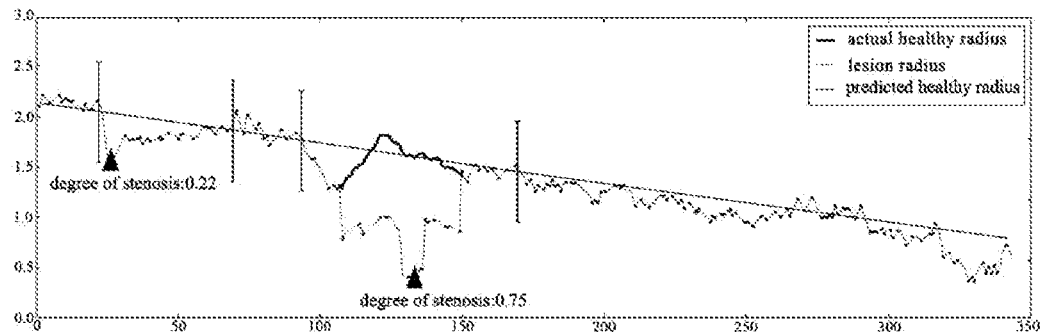
FIG. 2(b) shows a comparison of a healthy radius of the vessel diameter predicted by a second prediction method and the actually measured healthy radius and lesion radius, in accordance with another embodiment of the present disclosure.
Figure 2C:
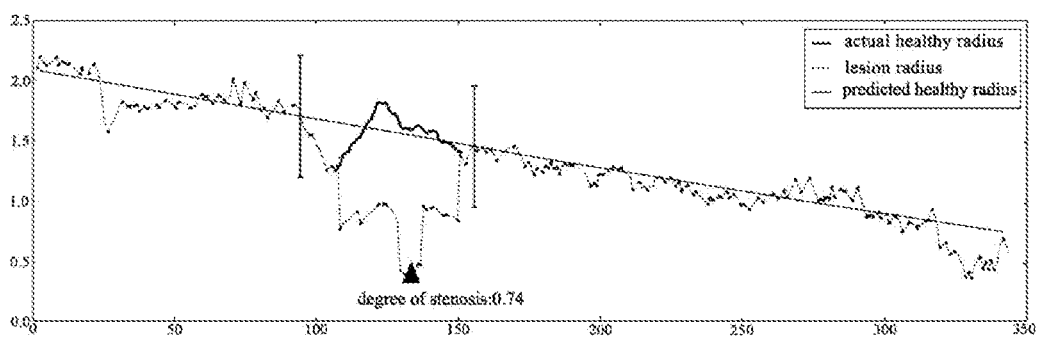
FIG. 2(c) shows a comparison of a healthy radius of the vessel diameter predicted by a third prediction method and actually measured healthy radius and lesion radius, in accordance with yet another embodiment of the present disclosure.

In some embodiments, a linear regression can also be performed on the peak of the radius in the blood vessel radius to predict the reference healthy radius of the vessel on the blood vessel path, and based on the reference healthy radius, the radius peak in the blood vessel radius can be processed. For example, a radius peak below the corresponding reference healthy radius is removed from the radius peak in the blood vessel radius (hereinafter referred to as "removal processing" for short), or the radius peak below the reference healthy radius is replaced with the corresponding reference healthy radius (hereinafter referred to as "replacement processing" for short). The healthy radius of the blood vessel on the blood vessel path is then predicted by performing a second regression on the radius peak in the processed blood vessel radius. The solid line in FIG. 2(b)

shows the healthy radius of the blood vessel path predicted by the "removal process", and the solid line in FIG. 2(c) shows the healthy radius of the blood vessel path predicted by the "replacement process". As shown, the former is higher than the actually measured healthy radius, the latter is moderate, looks more reasonable, and is in good agreement with the actual measured healthy radius distribution. Using the healthy radius of the blood vessel path predicted by the "removal process", two candidate stenoses (e.g. a stenosis with a degree of stenosis greater than 0.2) can be detected, and the degree of stenosis is a ratio of the difference between magnitude of the valley at the stenosis and the predicted healthy radius of the corresponding position to the predicted healthy radius of the corresponding position. The degrees of stenosis of the two stenosis are 0.22 and 0.75, respectively (see FIG. 2(b)). Using the healthy radius of the blood vessel path predicted by the "replacement treatment", a candidate stenosis can be detected, where the degree of stenosis of the stenosis is 0.74 (see FIG. 2(c)), and the doctors manually measured the same blood vessel. The results (the actual number of stenosis and the actual measured degree of stenosis) are more consistent with the latter.

Although the healthy radius of the blood vessel path may not directly yield medical diagnosis results, the healthy radius of the blood vessel path can serve as an intermediate parameter that plays an important role in diagnosis. For example, the healthy radius of the blood vessel path can be used to further detect stenosis in the blood vessel path, and can also be used to further detect the abnormal bumps in the blood vessel path and so on. In certain embodiments, these further detection steps are also performed by a processor of the device implementing the method. Additionally, yet further steps such as stenosis removal steps using, for example, angioplasty, may likewise be performed by a device using input provided from the preceding steps. Other computer-implemented medical intervention based on the preceding prediction and detection steps are also permitted.

As used herein, the technical term "candidate stenosis" refers to a place where a significant stenosis requiring medical intervention is likely to occur. For example, the likelihood of the significant stenosis occurring at the place may be greater than a predetermined threshold, such as 50%, 95%, or 99%. In some embodiments, a method for predicting a candidate stenosis of a blood vessel path is provided, the predictive method can employ a method for predicting a healthy radius of a blood vessel path in accordance with various embodiments of the present disclosure to predict the healthy radius of the blood vessel path, and the processor detects (a sequence of) the radius valley in the blood vessel radius of the blood vessel path acquired in step 101, and then determines the candidate stenosis based on the detected radius of the blood vessel path and the healthy radius.

Candidate stenosis can be determined in various ways based on the radius valley and the healthy radius of the detected blood vessel path. For example, assuming that n valleys are detected on the blood vessel path (n is a natural number), the radius at each valley is $r_i$ and the corresponding healthy radius is $h_i$ (i takes any natural number between 1 and n), the first ratio $r_i/h_i$ of the radius valley $r_i$ to the corresponding healthy radius $h_i$ can be determined, and if the first ratio $r_i/h_i$ is less than a first predetermined threshold (e.g., 0.8), it may be determined here as the candidate stenosis. In some embodiments, a second ratio $(h_i-r_i)/h_i$ may also be determined, and if the second ratio is greater than a second predetermined threshold (e.g., 0.2), then it may be determined here as a candidate stenosis.

Figure 3:
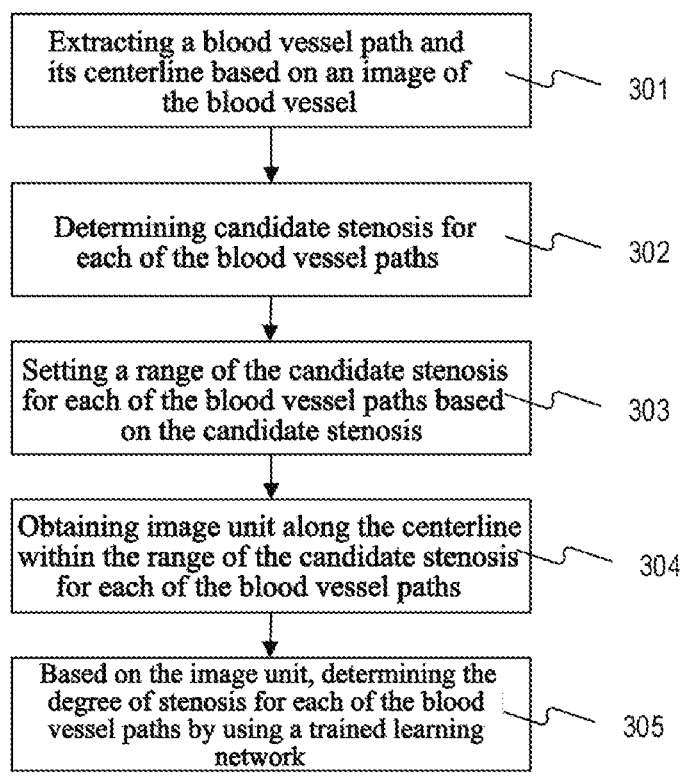
FIG. 3 illustrates a schematic diagram of a process for predicting a degree of stenosis of a blood vessel according to an embodiment of the present disclosure.

FIG. 3 shows a schematic diagram of a process 300 for predicting the degree of vessel stenosis in accordance with an embodiment of the present disclosure. The prediction process 300 may begin with receiving a medical image (not shown) of a blood vessel such as a blood vessel tree, which may be, for example, a CT image of a blood vessel tree, exemplified below by taking a CT image of a blood vessel tree as an example. The blood vessel path and its centerline may be extracted based on a CT image of the blood vessel tree using open source software such as VMTK or using existing vessel reconstruction software (step 301). The blood vessel tree may include multiple branches and thus may also include the blood vessel tree vessel path, and each blood vessel path has a corresponding centerline. In some embodiments, a 3D geometric model of each blood vessel path can be reconstructed by extracting a centerline and a vessel wall, and a sequence of vessel radii along the centerline is extracted from the geometric model. In some embodiments, the extraction of the vessel radius along the centerline does not necessarily reconstruct a 3D geometric model of the blood vessel path; for example, the blood vessel radius may also be determined from CT images along the centerline, such as via image analysis.

At step 302, the various stenosis of each blood vessel path can be determined using various methods described above. For example, for each blood vessel path, the candidate stenosis can be determined based on the sequence of blood vessel radii along its centerline. At step 303, the range of the candidate stenosis for each blood vessel path may be set based on the determined candidate stenosis. For example, the range of candidate stenosis can be set to a length centered at the determined candidate stenosis. In some embodiments, the range of candidate stenosis may be set to a length that is centered at the candidate stenosis point and that includes all points on both sides where the blood vessel radii $r_i$ is less than the corresponding healthy radius $h_i$.

Next, image units along the centerline within the candidate stenosis range of each blood vessel path can be acquired (step 304). These image units along the centerline can reflect the spatial geometry of the blood vessel path, for example, can be an image block taken along the centerline, or in a 3D model block sampled in a 3D model of the reconstructed vessel tree along the centerline.

In step 305, image units along the centerline (such as but not limited to image blocks) within the range of candidate stenosis of the acquired individual blood vessel paths may be taken as an input of the model and fed into the trained learning network to determine the stenosis of the corresponding blood vessel path. By predicting the degree of stenosis for the range of candidate stenosis for the blood vessel path, the search space can be significantly reduced, the prediction efficiency can be improved, the computational load can be reduced, and the computation speed can be increased. Moreover, taking advantage of the predicted healthy radius that is highly consistent with the actual measured value, the range of candidate stenosis in which significant stenosis may occur can be extracted from the entire blood vessel path, thereby ensuring the detection rate and reducing the missed detection rate. The setting of the range of candidate stenosis and the prediction of the degree of stenosis within the range can be automatically realized with the manual intervention significantly reduced. In practice, the labor burden of the hospital can be alleviated, and the dependence on the doctor's experience may be significantly reduced, which may be beneficial to rapid and wide clinical implementation.

Figure 4:
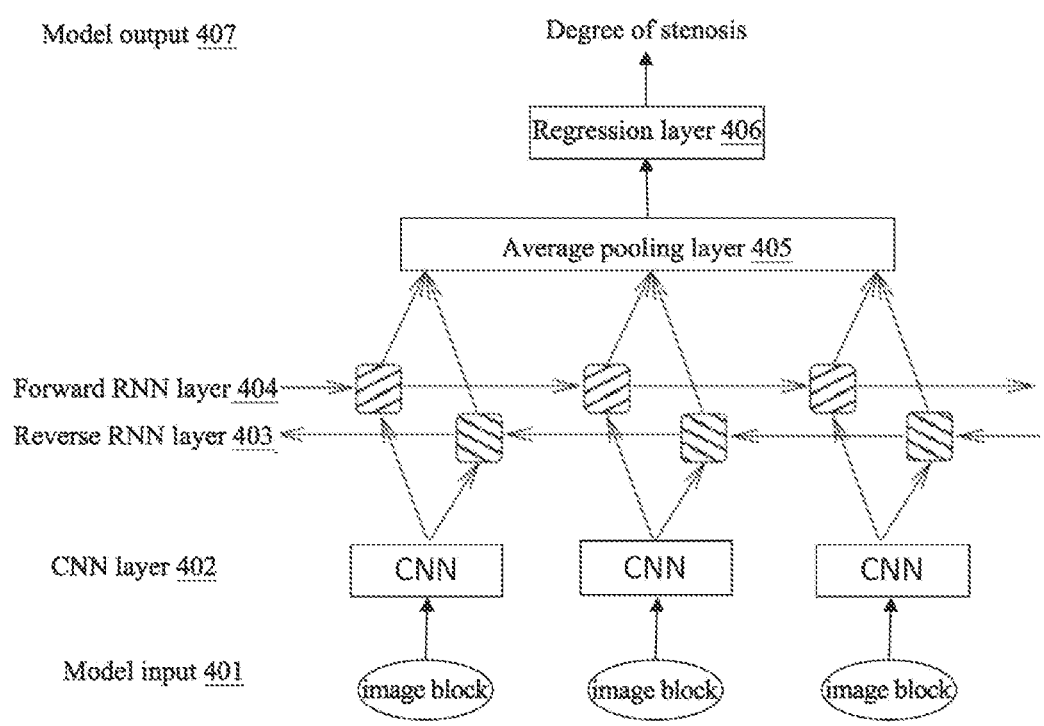
FIG. 4 illustrates a structural diagram of a learning network for predicting a degree of stenosis of a blood vessel according to an embodiment of the present disclosure.

FIG. 4 illustrates a structural diagram of a learning network for predicting a degree of stenosis of a blood vessel according to an embodiment of the present disclosure. As shown in FIG. 4, the learning network can be constructed based on a convolutional neural network (CNN) and a recurrent neural network (RNN). An example is taken using an image block along a centerline as a model input. The learning network is an end-to-end learning model from an image block along the centerline to a stenosis along the centerline. An image block along the centerline ($x_t$, t may take any natural number between 1 and the total number of sample points T) may be fed as a model input 401 to a corresponding CNN unit of the CNN layer 402, and the CNN unit acts as an encoder to learn and encode the image block $x_t$ to learn local and spatial information and produce a vector $z_t = V(x_t)$ of fixed length. The vector $z_t$ is then fed into the recurrent neural network. In some embodiments, the recurrent neural network can include a forward RNN layer 404, a reverse RNN layer 403, an average pooling layer 405, and a regression layer 406. The vector z can be fed into the bidirectional RNN layer including the forward RNN layer 404 and the reverse RNN layer 403 to simultaneously learn a correlation in the key positive and negative directions of the sequence data (for the points on the blood vessel path, between the upstream and downstream points) using the forward RNN layer 404 and the reverse RNN layer 403. The forward RNN layer 404 and the reverse RNN layer 403 of the bidirectional RNN layer are not connected by edges, and can be separately trained by the general RNN training method, and their computations can be processed in parallel, which helps to improve computational efficiency. Subsequently, it is fed into the average pooling layer 405 for up-sampling to extend the field of view of the prediction model to yield a more robust result. Here, the average pooling layer is used as an example, but other up-sampling layers, such as a maximum pooling layer, etc., may also be employed. The up-sampled data using the average pooling layer 405 is fed to the regression layer 406 to ultimately predict the degree of stenosis at various positions of the blood vessel path.

In FIG. 4, hatching is used to identify each node in the RNN layer. According to different requirements, each node can use long-term and short-term memory (LSTM) recurrent neural network, gated recursive unit (GRU), bidirectional LSTM recurrent neural network, and bidirectional GRU and the like. The bidirectional RNN can take into account the relationship between the detection point and its upstream and downstream detection points, and can improve the prediction accuracy of the degree of stenosis.

Figure 5:
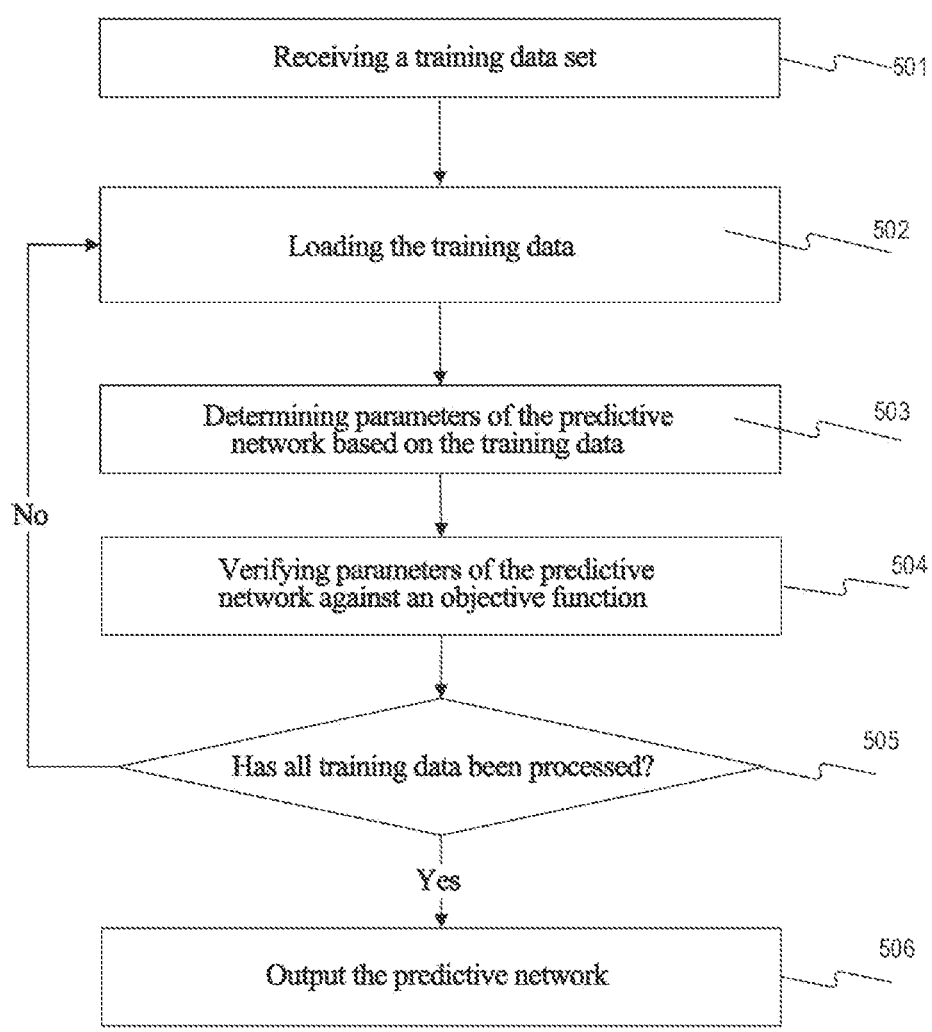
FIG. 5 illustrates a flow diagram for training a learning network for predicting a degree of stenosis of blood vessels in accordance with an embodiment of the present disclosure.

FIG. 5 shows an illustration of a training process 500 for training a learning network for predicting degree of stenosis of blood vessels in accordance with an embodiment of the present disclosure. The training process begins with receiving a training data set (step 501), taking an image block along the centerline as a model input, and each pair of data in the training data set is an image block $\langle x_1, x_2, \ldots, x_T \rangle$ taken along T sampling points along the centerline and the artificially labeled degree of stenosis $\langle y_1, y_2, \ldots, y_T \rangle$ (ground truth) at the corresponding position. At step 502, the received training data set may be loaded (e.g., all loaded or loaded in batch) as current training data (step 502).

The parameters of the predictive network may be determined based on the training data (step 503) and verified against an objective function (step 504) to optimize the parameters for the training data. In some embodiments, the parameters of the predictive network may include at least one of the number of network layers in the CNN portion, the number of nodes per layer network, the number of hidden layers in the RNN portion, a learning rate, and an initial value. The optimal value of these parameters can be determined by cross-validation. As mentioned above, the predictive network can be constructed by connecting the CNN encoder to the corresponding node of the bidirectional RNN. Thus, the predictive network may contain parameters (V, W) where the parameter V is for the CNN encoder portion and the parameter W is for the bidirectional RNN portion. In some embodiments, the parameters (V, W) can be jointly optimized by minimizing the objective function. In some embodiments, the objective function can be:

$$L = -\frac{1}{|D|} \sum_{(x_t, y_t)_{t=1}^T \in D} \sum_{t=1}^{T} \log P(y_t \mid x_{1:t}, y_{1:t-1}, V, W),$$

Where D represents the training data set, |D| represents the number of samples in the training set, T represents the length of each sample in the training set, P represents the probability, back propagation can be used to calculate the gradient $\nabla_{V,W} L(V, W)$, and the stochastic gradient descent method is used to optimize the parameters (V, W).

Although the stochastic gradient descent method and the objective function L are disclosed as examples, other objective functions may be employed, including but not limited to cross entropy, etc., and other parameter optimization methods, including but not limited to adaptive moment estimation, etc., may also be employed. After confirming that all training data has been processed in step 505, a predictive network whose parameters have been optimized on all training data may be output (step 506). In some embodiments, the training of the predictive network may also be ended after the convergence of the objective function is confirmed. In some embodiments, a regularization method of L1 or L2 can also be used to avoid over-fitting. In some embodiments, the training data set can also be divided into batches and trained using a small batch gradient descent method to reduce computational load while avoiding over-fitting.

Figure 6:
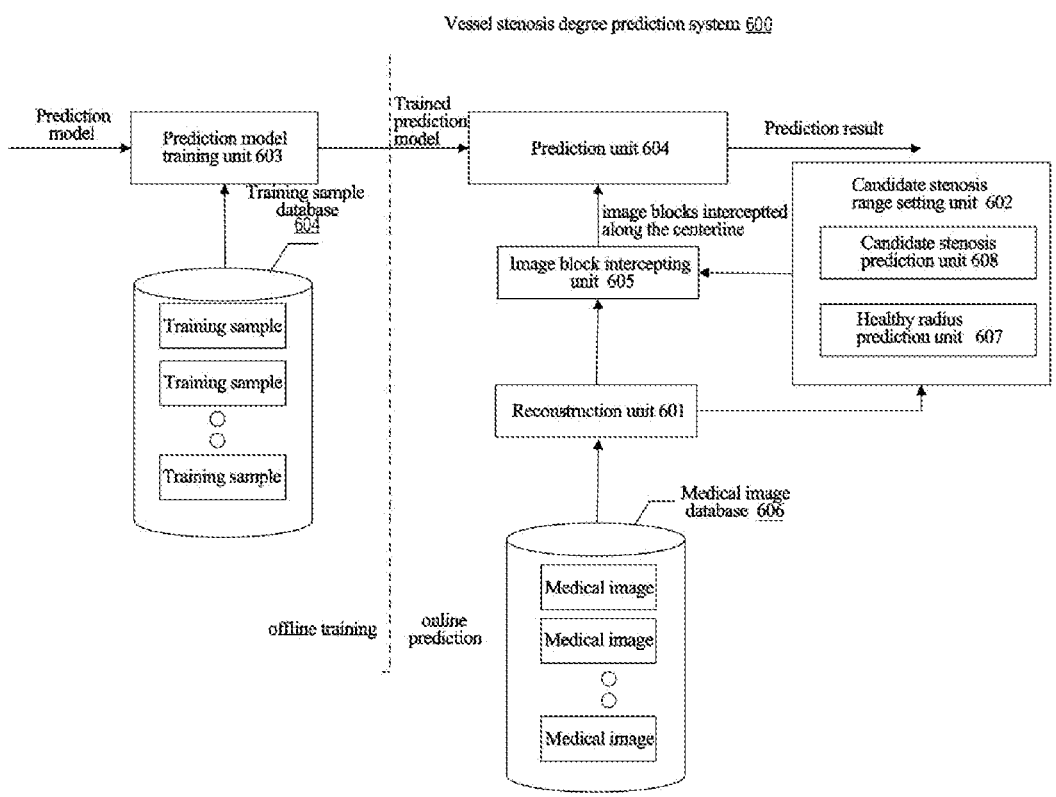
FIG. 6 shows a schematic illustration of a system for predicting a degree of stenosis of blood vessel in accordance with an embodiment of the present disclosure.

FIG. 6 shows a schematic illustration of a vessel stenosis degree prediction system 600 in accordance with an embodiment of the present disclosure. As shown in FIG. 6, the left side of the dashed line is the offline training process: the established prediction model is transmitted to the prediction model training unit 603, which trains the prediction model by using training samples from the training sample database 604. Each training sample can be composed of image blocks at a series of stenosis locations manually labeled by the physician on the blood vessel path on the vessel image and the degree of stenosis at the corresponding locations. Compared to the independent training of the various modules in the existing prediction model, training samples used for such end-to-end training are easier to acquire and build. The trained prediction model is fed into a prediction unit 604 to calculate a predicted result based on the model input. In some embodiments, the blood vessel path corresponding to the training sample conforms to the same or similar spatial relationship as the blood vessel path as the stenosis degree prediction target (e.g., the number of sampling points and the spatial constraint relationship between the sampling points), such that the trained prediction model can be seamlessly interfaced with the predicted target without the need for conversion training and can further improve the accuracy of the prediction.

To the right of the dotted line is the online prediction process. First, a medical image of a patient is obtained from the medical image database 606, and a CT image satisfying the DICOM standard of the blood vessel tree will be described below as an example. It is noted that the medical image database 606 can be a database of patient medical images shared within the hospital or among the hospitals. The CT image of the blood vessel tree can be fed into a reconstruction unit 601, which can be developed, for example, using existing blood vessel reconstruction software, or by using open source software such as VMTK, to extract the centerline and blood vessel wall from the CT image of the blood vessel tree to reconstruct the geometric model of each blood vessel path (optionally reconstructing the blood vessel tree). The geometric model of the reconstructed blood vessel path may be fed to the image block intercepting unit 605 and the candidate stenosis range setting unit 602. The candidate stenosis range setting unit 602 includes a healthy radius prediction unit 607 and a candidate stenosis prediction unit 608, wherein the healthy radius prediction unit 607 can extract a blood vessel radius of the corresponding blood vessel path based on the reconstructed geometric model of each blood vessel path, and then the healthy radius of the blood vessel path may be predicted by using a method for predicting the healthy radius of the blood vessel path according to various embodiments of the present disclosure, and the candidate stenosis prediction unit 608 may obtain the blood vessel radius of the corresponding blood vessel path from the healthy radius prediction unit 607 and detect the radius therefrom radius valley, and the healthy radius of the predicted blood vessel path is then obtained from the healthy radius prediction unit 607, thereby determining the candidate stenosis by utilizing the method for predicting the candidate stenosis of the blood vessel path according to various embodiments of the present disclosure, based on the predicted healthy radius of the blood vessel path and the obtained radius valley of the blood vessel path. In some embodiments, the candidate stenosis range setting unit 602 may set a candidate stenosis range based on the determined candidate stenosis. For example, the candidate stenosis range may be set to a length including all points on both sides where blood vessel radii are smaller than the corresponding healthy radius with the candidate stenosis point being a center.

The image block intercepting unit 605 may receive the set candidate stenosis range from the candidate stenosis range setting unit 602, and intercept a certain number of image blocks along the centerline of the blood vessel within the candidate stenosis range from the reconstructed geometric model of the blood vessel path. The size of the image block can be preset according to user's needs and experience. In some embodiments, the prediction model is constructed based on a convolutional neural network and a recurrent neural network, and the number of image blocks may be preset to be the same as the number of nodes of the recurrent neural network, and the number of nodes of the recurrent neural network may be preset according to a user's needs and experience.

A certain number of image blocks intercepted by the image block intercepting unit 605 along the centerline may be fed into a prediction unit 604, which may be configured to predict the degree of stenosis of the corresponding blood vessel path using the trained prediction model based on the acquired image block sequence.

Figure 7:
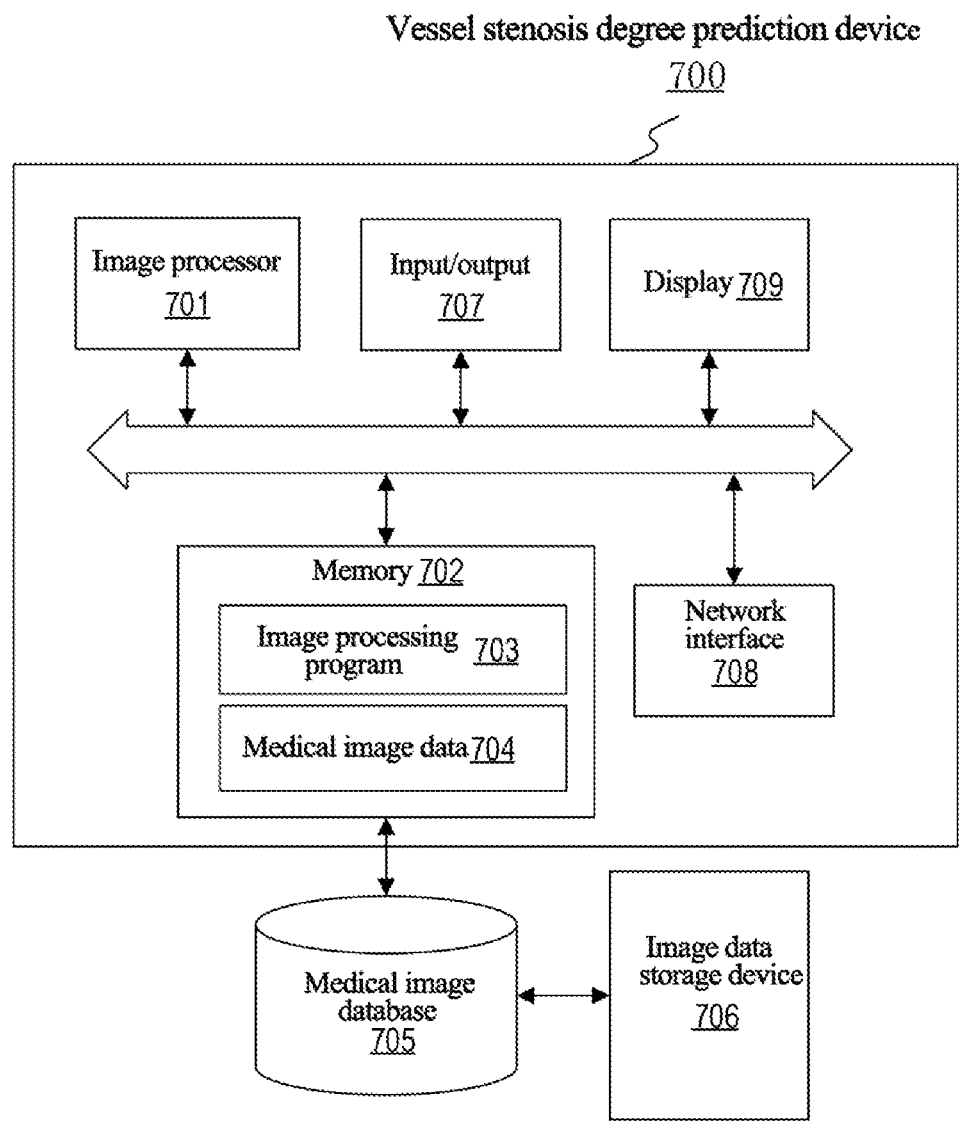
FIG. 7 shows a block diagram of a device for predicting a degree of stenosis of blood vessel according to an embodiment of the present disclosure.

FIG. 7 shows a schematic block diagram of a blood vessel stenosis degree prediction device 700 according to an embodiment of the present disclosure. The vessel stenosis degree prediction device 700 can include a network interface 708 via which the vessel stenosis degree prediction device 700 can be connected to a network (not shown), such as, but not limited to, a local area network or the Internet in a hospital. The network may connect the blood vessel stenosis degree prediction device 700 to an external device such as an image acquisition device (not shown), a medical image database 705, and an image data storage device 706.

In some embodiments, anatomical tree structure analysis device 700 can be a dedicated smart device or a general-purpose smart device. For example, the device 700 can be a computer customized for image data acquisition and image data processing tasks, or a server located in the cloud. For example, device 700 can be integrated into an image acquisition device. Alternatively, the (at least one) image processing program 703 in the device 700 may comprise or cooperate with a 3D reconstruction unit for reconstructing a 3D model of the blood vessel based on the 2D blood vessel image acquired by the image acquisition device, and the image blocks may be extracted from the 3D model as a model input at a set of centerline points.

The blood vessel stenosis degree prediction device 700 may include an image processor 701 and a memory 702, and may additionally include at least one of an input/output 707 and an image display 709.

The image processor 701 can be any of the processors described in various embodiments of the present disclosure. The disclosed embodiments are not limited to any type of processor or processor circuit that is otherwise configured to satisfy the computational requirements for identifying, analyzing, maintaining, generating, and/or providing a large amount of imaging data or manipulating such imaging data or manipulating any other type of data in consistent with the disclosed embodiments. Additionally, the term "processor" or "image processor" may include more than one processor, such as a multi-core design or multiple processors, each having a multi-core design. The image processor 701 can execute a sequence of computer program instructions stored in the memory 702 to perform the various operations, processes, and methods disclosed herein.

The image processor 701 can be communicatively coupled to the memory 702 and configured to execute computer executable instructions stored therein. The memory 702 may include read only memory (ROM), flash memory, random access memory (RAM), dynamic random access memory (DRAM) such as synchronous DRAM (SDRAM) or Rambus DRAM, static memory (e.g. flash memory, static random access memory) and the like, and computer executable instructions are stored therein in any format. In some embodiments, the memory 702 can store computer-executable instructions of one or more image processing programs 703. Computer program instructions may be accessed by image processor 701, read from ROM or any other suitable memory location, and loaded into RAM for execution by image processor 701. For example, the memory 702 can store one or more software applications. The software applications stored in the memory 702 may include, for example, an operating system (not shown) for a general computer system and an operating system for the soft control device.

Moreover, the memory 702 can store the entire software application or only a portion of the software application (e.g. image processing program 703) that can be executed by the image processor 701. In addition, the memory 702 can store a plurality of software modules for implementing various steps of various methods consistent with the present disclosure for predicting a healthy radius of a blood vessel path, predicting a candidate stenosis of a blood vessel path, and predicting a degree of stenosis of a blood vessel path. For example, the prediction model training unit 603, the prediction unit 604, the image block intercepting unit 605, the reconstruction unit 601, and the candidate stenosis range setting unit 602 (as shown in FIG. 6) may be implemented as software modules stored on the memory 702. As another example, at least the prediction unit 604, the image block intercepting unit 605, the reconstruction unit 601, and the candidate stenosis range setting unit 602 may be implemented as a software module stored in the memory 702. The prediction model training unit 603 may be located away from the blood vessel stenosis degree prediction device 700, and can be communicated with the prediction unit 604 to enable it to receive an updated prediction model that can be trained by prediction model training unit 603 using training samples from training sample database 604 (in an offline training process) and/or training samples from the prediction unit 604 (i.e., the stenosis degree prediction results along with the image blocks extracted at the corresponding locations) (in the online training process).

Moreover, memory 702 can store data generated/cached when the computer program is executed, for example, medical image data 704, including medical images transmitted from image acquisition device, medical image database 705, image data storage device 706, and the like. In some embodiments, the medical image data 704 can include an image of the received vessel tree, and the (at least one) image processing program 703 implements centerline extraction and 3D model reconstruction, image block extraction (as a model input) and prediction of degree of blood vessel stenosis for the image of the vessel tree. In some embodiments, the medical image data 704 can include a volumetric image of the received vessel tree, and the (at least one) image processing program 703 is to perform an image block extraction along the centerline for the volumetric image of the vessel tree (as a model input) and prediction of degree of blood vessel stenosis. In some embodiments, the memory 702 can load a batch of training samples from the medical image database 705 and temporarily store it as medical image data 704 for use by prediction model training unit 603 for small batch training. In some embodiments, memory 702 can temporarily store prediction results and corresponding model inputs as online training samples. The training samples stored as the medical image data 704 can be deleted after the training with them is completed so as to free up the space of the memory 702 and increase its capacity and performance.

In some embodiments, the prediction model can be stored in the medical image data 704, and be used in the next prediction of degree of blood vessel stenosis (used after training). In some embodiments, the updated and optimized parameters of the trained prediction model can be stored in the medical image data 704, and can be utilized in the next prediction of degree of blood vessel stenosis of the corresponding blood vessel path of the same patient.

In some embodiments, the image processor 701, after predicting the stenosis distribution of the blood vessel path, can associate the image of the blood vessel tree with the predicted result as medical image data 704 for presentation and/or transmission. In some embodiments, an image of the vessel tree along with the predicted results can be displayed on image display 709 for viewing by the user. For example, the image display 709 can be an LCD, CRT, or LED display. The input/output 707 may provide medical image data 704 to the display 709. In this way, the user can utilize input/output 707 to confirm and correct the displayed predictions, if desired. The confirmed and corrected blood vessel stenosis prediction result may be temporarily stored in the memory 702 as medical image data 704 in association with a model input such as an image block along the center line, and may be transmitted to the medical image database 705 for being accessed, obtained and used by another medical device (such as other anatomical tree structure analysis device 700) as needed.

In some embodiments, the memory 702 can be in communication with the medical image database 705 to transmit and save the extracted model input into the medical image database 705 in association with the prediction results as a piece of training data that can be used for offline training. In this manner, the training sample database 604 as shown in FIG. 6 can be incorporated into the medical image database 705.

In addition, the parameters of the trained prediction model can be stored in the medical image database 705 for access and acquisition. The parameters of the trained prediction model can be used by other vessel stenosis degree prediction devices 700, if desired.

In some embodiments, the medical image database 606 shown in FIG. 6 can be included into the medical image database 705, which can maintain medical images and/or 3D models and/or centerlines and/or a series of image blocks along the centerline of the vessel tree according to the patient. Thus, the memory 702 can communicate with the medical image database 705 to obtain at least one of a medical image, a 3D model, a centerline, and a series of image blocks along the centerline of the current user's vessel tree. The 3D model, the centerline, and a series of image blocks along the centerline of the vessel tree can be constructed and extracted by the reconstruction unit 601 shown in FIG. 6, and transmitted to the medical image database 705 for storage by the user.

In some embodiments, image data storage device 706 can be provided to exchange image data with the medical image database 705. For example, the image data storage device 706 can reside in other medical image acquisition devices, such as a CT that performs a volumetric scan of a patient. The patient's volumetric image can be transmitted and saved into the medical image database 705, and the vessel stenosis degree prediction device 700 can take a volumetric image and a prediction model of the particular patient from the medical image database 705 and make a prediction of degree of stenosis based thereon.

The input/output 707 can be configured to allow blood vessel stenosis degree prediction device 700 to receive and/or transmit data. Input/output 707 may include one or more digital and/or analog communication devices that allow device 700 to communicate with a user or other machine(s) and device(s). For example, input/output 707 can include a keyboard and mouse that allow a user to provide input.

The network interface 708 may include a network adapter, a cable connector, a serial connector, a USB connector, a parallel connector, a high speed data transfer adapter such as fiber optics, USB 6.0, lightning, a wireless network adapter such as a Wi-Fi adapter, telecommunications (6G, 4G/LTE, etc.) adapters. Device 700 can be connected to the network via network interface 708. The network may provide functions such as a local area network (LAN), a wireless network, a cloud computing environment (e.g. software as a service, a platform as a service, an infrastructure as a service, etc.), a client-server, a wide area network (WAN), and the like.

The various steps, operations, or functions described above may be implemented or defined as software code or instructions. Such content may be directly executable ("object" or "executable" form), source code or differential code ("delta" or "patch" code). The software implementation of the embodiments described herein may be provided via an article having code or instructions stored thereon or via a method of operating a communication interface to transmit data via a communication interface. For example, a non-transitory computer-readable medium can encode instructions that, when executed in hardware, perform a process, including any of the various steps, operations, or functions described above.

Execution of the order or operation of the embodiments of the present invention shown and described herein is not essential, unless otherwise indicated. That is, operations may be executed in any order, unless otherwise stated, and embodiments of the invention may include more or fewer operations than those disclosed herein. For example, executing or implementing a particular operation before, concurrently with, or after another operation is contemplated to be within the scope of the inventive arrangements.

Embodiments of the invention may be implemented using computer executable instructions. Computer executable instructions can be organized into one or more computer executable components or modules. The various aspects of the invention can be implemented using any number and organization of such components or modules. For example, aspects of the invention are not limited to the specific computer-executable instructions or specific components or modules shown in the drawings and described herein. Other embodiments of the invention may include different computer-executable instructions or components having more or less functionality than those illustrated and described herein.

The various aspects of the present invention have been described in detail, and it is obvious that modifications and variations are possible without departing from the scope of the invention as defined in the appended claims. Since various changes to the above-described structures, products, and methods can be made without departing from the scope of the present invention, it is intended that all of the contents included in the above description and shown in the drawings should be construed as exemplary without restrictive meaning.

What is claimed is:

1. A computer-implemented method for predicting a blood vessel stenosis, the method comprising:
   extracting a blood vessel path and its centerline based on an image of a blood vessel;
   determining a candidate stenosis for the blood vessel path;
   identifying image blocks along the centerline of the blood vessel path within a range of candidate stenosis for the blood vessel path determined based on the candidate stenosis; and
   determining a degree of stenosis for the blood vessel path by applying a trained learning network comprising a convolutional neural network and a recurrent neural network on the image blocks within the range of candidate stenosis,
   wherein the convolutional neural network and the recurrent neural network are sequentially applied, wherein the convolutional neural network is applied on the image blocks along the centerline of the blood vessel path to generate vectors for the respective image blocks, wherein the recurrent neural network is applied on the vectors.

2. The computer-implemented method according to claim 1, further comprising:
   predicting a healthy radius of the blood vessel path by performing a quadratic regression on blood vessel radius peaks of the blood vessel path; and
   determining the candidate stenosis for the blood vessel path based on the healthy radius of the blood vessel path.

3. The computer-implemented method according to claim 2, wherein predicting the healthy radius of the blood vessel path further comprises:
   predicting a reference healthy radius of the blood vessel path by performing a linear regression on the blood vessel radius peaks; and
   replacing the blood vessel radius peaks in the blood vessel path that are lower than the reference healthy radius with the reference healthy radius.

4. The computer-implemented method according to claim 1, wherein the range of candidate stenosis for the blood vessel path has the candidate stenosis at its center.

5. The computer-implemented method according to claim 1, wherein the convolutional neural network and the recurrent neural network are jointly trained.

6. The computer-implemented method according to claim 1, wherein the convolutional neural network comprises a plurality of convolutional neural network units each configured to process one of the image blocks along the centerline of the blood vessel path.

7. The computer-implemented method according to claim 1, wherein the recurrent neural network comprises a forward recurrent neural network and a reverse recurrent neural network configured to collectively learn a spatial correlation among the image blocks along the centerline of the blood vessel path.

8. The computer-implemented method according to claim 7, wherein the forward recurrent neural network and the reverse recurrent neural network are separately trained.

9. The computer-implemented method according to claim 1, further comprising outputting at least one of the candidate stenosis, the range of candidate stenosis, and the degree of stenosis of the blood vessel path.

10. A blood vessel stenosis degree prediction system, comprising:
    an interface configured to receive an image of a blood vessel;
    a processor configured to:
      extract a blood vessel path and its centerline based on the image of the blood vessel;
      determine a candidate stenosis for the blood vessel path;
      identify image blocks along the centerline of the blood vessel path within a range of candidate stenosis for the blood vessel path determined based on the candidate stenosis; and
      determine a degree of stenosis for the blood vessel path by applying a trained learning network comprising a convolutional neural network and a recurrent neural network on the image blocks within the range of candidate stenosis,
      wherein the convolutional neural network and the recurrent neural network are sequentially applied, wherein the convolutional neural network is applied on the image blocks along the centerline of the blood vessel path to generate vectors for the respective image blocks, wherein the recurrent neural network is applied on the vectors.

11. The blood vessel stenosis degree prediction system according to claim 10, wherein the processor is further configured to:
predict a healthy radius of the blood vessel path by performing a quadratic regression on blood vessel radius peaks of the blood vessel path; and
determine the candidate stenosis for the blood vessel path based on the healthy radius of the blood vessel path.

12. The blood vessel stenosis degree prediction system according to claim 10, wherein to predict the healthy radius of the blood vessel path, the processor is further configured to:
predict a reference healthy radius of the blood vessel path by performing a linear regression on the blood vessel radius peaks; and
replace the blood vessel radius peaks in the blood vessel path that are lower than the reference healthy radius with the reference healthy radius.

13. The blood vessel stenosis degree prediction system according to claim 10, wherein the range of candidate stenosis for the blood vessel path has the candidate stenosis at its center.

14. The blood vessel stenosis degree prediction system according to claim 10, wherein the convolutional neural network and the recurrent neural network are jointly trained.

15. The blood vessel stenosis degree prediction system according to claim 10, wherein the recurrent neural network comprises a forward recurrent neural network and a reverse recurrent neural network configured to collectively learn a spatial correlation among the image blocks along the centerline of the blood vessel path.

16. The blood vessel stenosis degree prediction system according to claim 15, wherein the forward recurrent neural network and the reverse recurrent neural network are separately trained.

17. The blood vessel stenosis degree prediction system according to claim 10, further comprising a display configured to output at least one of the candidate stenosis, the range of candidate stenosis, and the degree of stenosis of the blood vessel path.

18. The blood vessel stenosis degree prediction system according to claim 10, wherein the convolutional neural network comprises a plurality of convolutional neural network units each configured to process one of the image blocks along the centerline of the blood vessel path.

19. A non-transitory storage medium having stored thereon computer executable instructions that, when executed by a processor, implement a method for predicting a blood vessel stenosis, the method comprising:
extracting a blood vessel path and its centerline based on an image of a blood vessel;
determining a candidate stenosis for the blood vessel path;
identifying image blocks along the centerline of the blood vessel path within a range of candidate stenosis for the blood vessel path determined based on the candidate stenosis; and
determining a degree of stenosis for the blood vessel path by applying a trained learning network comprising a convolutional neural network and a recurrent neural network on the image blocks within the range of candidate stenosis,
wherein the convolutional neural network and the recurrent neural network are sequentially applied, wherein the convolutional neural network is applied on the image blocks along the centerline of the blood vessel path to generate vectors for the respective image blocks, wherein the recurrent neural network is applied on the vectors.

20. The non-transitory storage medium according to claim 19, wherein the method further comprises outputting at least one of the candidate stenosis, the range of candidate stenosis, and the degree of stenosis of the blood vessel path.

* * * * *